US012616603B2

(12) United States Patent
Hansen et al.

(10) Patent No.: US 12,616,603 B2
(45) Date of Patent: May 5, 2026

(54) SENSOR PATCH FOR ATTACHMENT TO A BASE PLATE

(71) Applicant: Coloplast A/S, Humlebaek (DK)

(72) Inventors: Jais Ask Hansen, Jaegerspris (DK); Lars Molzen, Kongens Lyngby (DK); Lars Stendevad Windeballe, Virum (DK); Esben Stroebech, Hoersholm (DK); Kamilla Grove Sund, Alleroed (DK)

(73) Assignee: Coloplast A/S, Humlebaek (DK)

( * ) Notice: Subject to any disclaimer, the term of this patent is extended or adjusted under 35 U.S.C. 154(b) by 1074 days.

(21) Appl. No.: 17/606,055

(22) PCT Filed: Apr. 24, 2020

(86) PCT No.: PCT/DK2020/050113
§ 371 (c)(1),
(2) Date: Oct. 25, 2021

(87) PCT Pub. No.: WO2020/216427
PCT Pub. Date: Oct. 29, 2020

(65) Prior Publication Data
US 2022/0192860 A1 Jun. 23, 2022

(30) Foreign Application Priority Data

Apr. 26, 2019 (DK) ............................ PA 2019 70261

(51) Int. Cl.
*A61F 5/445* (2006.01)
*A61F 5/44* (2006.01)
*A61F 5/443* (2006.01)

(52) U.S. Cl.
CPC ............ *A61F 5/445* (2013.01); *A61F 5/4404* (2013.01); *A61F 5/443* (2013.01)

(58) Field of Classification Search
CPC ......... A61F 5/445; A61F 5/4404; A61F 5/443
See application file for complete search history.

(56) References Cited

U.S. PATENT DOCUMENTS

| | | | |
|---|---|---|---|
| 2,327,514 A | 8/1943 | Fenwick | |
| 2,542,233 A | 2/1951 | Carroll | |
| | (Continued) | | |

FOREIGN PATENT DOCUMENTS

| | | | |
|---|---|---|---|
| AU | 2007342523 B2 | 7/2011 | |
| CA | 2540756 C | 1/2008 | |
| | (Continued) | | |

*Primary Examiner* — Rebecca E Eisenberg
*Assistant Examiner* — Gabriella E Burnette
(74) *Attorney, Agent, or Firm* — Coloplast Corp., Coloplast A/S; Nick Baumann

(57) ABSTRACT

A sensor patch (10) for attachment to a base plate for an ostomy appliance, where the sensor patch comprises a distal side and a proximal side comprising at least one adhesive layer (15), a part of the distal side being adapted for attachment to the base plate and the proximal adhesive side being adapted to adhere to the skin surface of a user, where the sensor patch comprises two or more electrodes (12) and a monitor interface (13) for forming a connection to a monitor device, and where the sensor patch comprises a central portion and a neck portion, the electrodes extending from the central portion to the neck portion, the neck portion comprising a flexible element being adapted to allow the central portion and the neck portion to be flexibly movable relative to each other.

12 Claims, 7 Drawing Sheets

(56) References Cited

U.S. PATENT DOCUMENTS

| | | | |
|---|---|---|---|
| 2,544,579 A | 3/1951 | Ardner | |
| 3,214,502 A | 10/1965 | Schaar | |
| 3,808,354 A | 4/1974 | Feezor et al. | |
| 3,832,510 A | 8/1974 | Pfau et al. | |
| 3,915,171 A | 10/1975 | Shermeta | |
| 3,941,133 A | 3/1976 | Chen | |
| 4,231,369 A | 11/1980 | Sorensen et al. | |
| 4,372,308 A | 2/1983 | Steer et al. | |
| 4,449,970 A | 5/1984 | Bevan et al. | |
| 4,668,227 A | 5/1987 | Kay | |
| 4,754,264 A | 6/1988 | Okada et al. | |
| 4,775,374 A | 10/1988 | Cilento et al. | |
| 4,834,731 A | 5/1989 | Nowak et al. | |
| 4,973,323 A | 11/1990 | Kaczmarek et al. | |
| 4,982,742 A | 1/1991 | Claude | |
| 5,013,307 A | 5/1991 | Broida | |
| 5,016,645 A | 5/1991 | Williams et al. | |
| 5,051,259 A | 9/1991 | Olsen et al. | |
| 5,074,851 A | 12/1991 | Plass et al. | |
| 5,111,812 A | 5/1992 | Swanson et al. | |
| 5,147,343 A | 9/1992 | Kellenberger | |
| 5,237,995 A | 8/1993 | Cano | |
| 5,318,543 A | 6/1994 | Ross et al. | |
| 5,322,797 A | 6/1994 | Mallow et al. | |
| 5,358,488 A | 10/1994 | Suriyapa | |
| 5,486,158 A | 1/1996 | Samuelsen | |
| 5,519,644 A | 5/1996 | Benton | |
| 5,570,082 A | 10/1996 | Mahgerefteh et al. | |
| 5,593,397 A | 1/1997 | La Gro | |
| 5,626,135 A | 5/1997 | Sanfilippo | |
| 5,672,163 A | 9/1997 | Ferreira et al. | |
| 5,677,221 A | 10/1997 | Tseng | |
| 5,704,905 A | 1/1998 | Jensen et al. | |
| 5,714,225 A | 2/1998 | Hansen et al. | |
| 5,790,036 A | 8/1998 | Fisher et al. | |
| 5,800,415 A | 9/1998 | Olsen | |
| 5,816,252 A | 10/1998 | Faries et al. | |
| 5,834,009 A | 11/1998 | Sawers et al. | |
| 5,846,558 A | 12/1998 | Nielsen et al. | |
| 5,876,855 A | 3/1999 | Wong et al. | |
| 5,879,292 A | 3/1999 | Sternberg et al. | |
| 5,942,186 A | 8/1999 | Sanada et al. | |
| 6,015,399 A | 1/2000 | Mracna et al. | |
| 6,025,725 A | 2/2000 | Gershenfeld et al. | |
| 6,078,261 A | 6/2000 | Davsko | |
| 6,093,276 A | 7/2000 | Leise, Jr. et al. | |
| 6,101,867 A | 8/2000 | Cavestri | |
| 6,103,033 A | 8/2000 | Say et al. | |
| 6,135,986 A | 10/2000 | Leisner et al. | |
| 6,171,289 B1 * | 1/2001 | Millot | A61F 5/443 |
| | | | 604/336 |
| 6,206,864 B1 | 3/2001 | Kavanagh et al. | |
| 6,241,704 B1 | 6/2001 | Peterson et al. | |
| 6,270,445 B1 | 8/2001 | Dean, Jr. et al. | |
| 6,297,422 B1 | 10/2001 | Hansen et al. | |
| 6,407,308 B1 | 6/2002 | Roe et al. | |
| 6,433,244 B1 | 8/2002 | Roe et al. | |
| 6,433,695 B1 | 8/2002 | Kai et al. | |
| 6,482,491 B1 | 11/2002 | Samuelsen et al. | |
| 6,485,476 B1 | 11/2002 | Von et al. | |
| 6,520,943 B1 | 2/2003 | Wagner | |
| 6,677,859 B1 | 1/2004 | Bensen | |
| 6,764,474 B2 | 7/2004 | Nielsen et al. | |
| 6,774,800 B2 | 8/2004 | Friedman et al. | |
| 7,014,816 B2 | 3/2006 | Miller et al. | |
| 7,049,478 B1 | 5/2006 | Smith | |
| 7,066,919 B1 | 6/2006 | Sauerland et al. | |
| 7,147,615 B2 * | 12/2006 | Wariar | G01N 27/121 |
| | | | 604/4.01 |
| 7,150,728 B2 | 12/2006 | Hansen et al. | |
| 7,166,091 B1 | 1/2007 | Zeltner | |
| 7,199,501 B2 | 4/2007 | Pei et al. | |
| 7,214,217 B2 | 5/2007 | Pedersen et al. | |
| 7,326,190 B2 | 2/2008 | Botten | |
| 7,341,578 B2 | 3/2008 | Bulow et al. | |
| 7,347,844 B2 | 3/2008 | Cline et al. | |
| 7,367,965 B2 | 5/2008 | Poulsen et al. | |
| 7,559,922 B2 | 7/2009 | Botten | |
| 7,625,362 B2 | 12/2009 | Boehringer et al. | |
| 7,641,612 B1 | 1/2010 | McCall | |
| 7,670,289 B1 | 3/2010 | McCall | |
| 7,943,812 B2 | 5/2011 | Stroebeck et al. | |
| 7,981,098 B2 | 7/2011 | Boehringer et al. | |
| 8,061,360 B2 | 11/2011 | Locke et al. | |
| 8,277,427 B2 | 10/2012 | Edvardsen et al. | |
| 8,319,003 B2 | 11/2012 | Olsen et al. | |
| 8,326,051 B1 | 12/2012 | Hobbs | |
| 8,343,437 B2 | 1/2013 | Patel | |
| 8,398,575 B1 | 3/2013 | Mccall | |
| 8,398,603 B2 | 3/2013 | Thirstrup et al. | |
| 8,399,732 B2 | 3/2013 | Delund et al. | |
| 8,409,158 B2 | 4/2013 | Edvardsen et al. | |
| 8,439,883 B1 | 5/2013 | Johnsen | |
| 8,449,471 B2 | 5/2013 | Tran | |
| 8,500,718 B2 | 8/2013 | Locke et al. | |
| 8,507,081 B2 | 8/2013 | Strobech et al. | |
| 8,632,492 B2 | 1/2014 | Delegge | |
| 8,680,991 B2 | 3/2014 | Tran | |
| 8,684,982 B2 | 4/2014 | Nguyen-Demary et al. | |
| 8,707,766 B2 | 4/2014 | Harris et al. | |
| 8,740,865 B2 | 6/2014 | Krystek et al. | |
| 8,795,257 B2 | 8/2014 | Coulthard et al. | |
| D712,545 S | 9/2014 | Igwebuike et al. | |
| 8,821,463 B2 | 9/2014 | Grum-Schwensen | |
| 8,821,464 B2 | 9/2014 | Hanuka et al. | |
| 8,975,465 B2 | 3/2015 | Hong et al. | |
| 8,978,452 B2 | 3/2015 | Johnson et al. | |
| 9,046,085 B2 | 6/2015 | Schoess et al. | |
| 9,066,812 B2 | 6/2015 | Edvardsen et al. | |
| 9,216,104 B2 | 12/2015 | Thirstrup et al. | |
| 9,308,332 B2 | 4/2016 | Heppe | |
| 9,322,797 B1 | 4/2016 | Lastinger et al. | |
| 9,506,886 B1 | 11/2016 | Woodbury et al. | |
| 9,566,383 B2 | 2/2017 | Yodfat et al. | |
| 9,629,964 B2 | 4/2017 | Wuepper | |
| 9,649,230 B1 | 5/2017 | Li | |
| 9,675,267 B2 | 6/2017 | Laakkonen et al. | |
| 9,693,908 B2 | 7/2017 | Eriksson et al. | |
| 9,770,359 B2 | 9/2017 | Edvardsen et al. | |
| 9,788,991 B2 | 10/2017 | Bird | |
| 9,867,934 B2 | 1/2018 | Heppe | |
| 9,928,341 B2 | 3/2018 | Angelides | |
| 10,016,298 B2 | 7/2018 | Thirstrup et al. | |
| 10,022,277 B2 | 7/2018 | Heil et al. | |
| D826,740 S | 8/2018 | Stevens et al. | |
| 10,426,342 B2 | 10/2019 | Hresko et al. | |
| 10,500,084 B2 | 12/2019 | Hansen et al. | |
| 10,531,977 B2 | 1/2020 | Schoess et al. | |
| 10,646,370 B2 | 5/2020 | Keleny et al. | |
| 10,792,184 B2 | 10/2020 | Hvid et al. | |
| 10,799,385 B2 | 10/2020 | Hansen et al. | |
| 10,849,781 B2 | 12/2020 | Hansen et al. | |
| 10,874,541 B2 | 12/2020 | Seres et al. | |
| 10,987,243 B2 | 4/2021 | Thirstrup et al. | |
| 11,096,818 B2 | 8/2021 | Thirstrup et al. | |
| 11,135,084 B2 | 10/2021 | Seres et al. | |
| 11,219,436 B2 | 1/2022 | Mayberg | |
| 11,238,133 B1 | 2/2022 | Brewer et al. | |
| 11,306,224 B2 | 4/2022 | Chatterjee et al. | |
| 11,406,525 B2 | 8/2022 | Seres et al. | |
| 11,471,318 B2 | 10/2022 | Hansen et al. | |
| 11,612,512 B2 | 3/2023 | Hansen et al. | |
| 11,903,728 B2 | 2/2024 | Svanegaard et al. | |
| 12,064,369 B2 | 8/2024 | Hansen et al. | |
| 2001/0041920 A1 | 11/2001 | Starkweather et al. | |
| 2001/0051787 A1 | 12/2001 | Haller et al. | |
| 2002/0013613 A1 | 1/2002 | Haller et al. | |
| 2002/0019615 A1 | 2/2002 | Roe et al. | |
| 2002/0109621 A1 | 8/2002 | Khair et al. | |
| 2003/0132763 A1 | 7/2003 | Ellenz | |
| 2003/0169032 A1 | 9/2003 | Minchole et al. | |
| 2004/0006320 A1 | 1/2004 | Buglino et al. | |
| 2004/0030305 A1 | 2/2004 | Sakamoto | |
| 2004/0036484 A1 | 2/2004 | Tamai | |

(56)　　　　References Cited

U.S. PATENT DOCUMENTS

| | | |
|---|---|---|
| 2004/0049145 A1 | 3/2004 | Flick |
| 2004/0068244 A1 | 4/2004 | Salone et al. |
| 2004/0078219 A1 | 4/2004 | Kaylor et al. |
| 2004/0100376 A1 | 5/2004 | Lye et al. |
| 2004/0106908 A1 | 6/2004 | Leise et al. |
| 2004/0133175 A1 | 7/2004 | Hagedorn-Olsen |
| 2004/0171999 A1 | 9/2004 | Andersen et al. |
| 2004/0193122 A1 | 9/2004 | Cline et al. |
| 2004/0193123 A1 | 9/2004 | Fenton |
| 2004/0216833 A1 | 11/2004 | Fleming et al. |
| 2005/0038325 A1 | 2/2005 | Moll |
| 2005/0054997 A1 | 3/2005 | Buglino et al. |
| 2005/0065488 A1 | 3/2005 | Elliott |
| 2005/0070863 A1 | 3/2005 | Bulow et al. |
| 2005/0085779 A1 | 4/2005 | Poulsen et al. |
| 2005/0101841 A9 | 5/2005 | Kaylor et al. |
| 2005/0240163 A1 | 10/2005 | Andersen |
| 2005/0256545 A1 | 11/2005 | Koh et al. |
| 2005/0261645 A1 | 11/2005 | Conrad et al. |
| 2006/0015081 A1 | 1/2006 | Suzuki et al. |
| 2006/0025727 A1 | 2/2006 | Boehringer et al. |
| 2006/0052752 A1 | 3/2006 | Mcmichael |
| 2006/0194324 A1 | 8/2006 | Faries et al. |
| 2006/0271002 A1 | 11/2006 | Botten |
| 2007/0035405 A1 | 2/2007 | Wada et al. |
| 2007/0135782 A1 | 6/2007 | Bager et al. |
| 2007/0185464 A1 | 8/2007 | Fattman et al. |
| 2007/0203407 A1 | 8/2007 | Hoss et al. |
| 2007/0204691 A1 | 9/2007 | Bogner et al. |
| 2008/0004580 A1 | 1/2008 | Mullejans et al. |
| 2008/0038536 A1 | 2/2008 | Strobech et al. |
| 2008/0041792 A1 | 2/2008 | Crnkovich et al. |
| 2008/0058740 A1 | 3/2008 | Sullivan et al. |
| 2008/0061965 A1 | 3/2008 | Kuhns et al. |
| 2008/0071214 A1 | 3/2008 | Locke et al. |
| 2008/0075934 A1 | 3/2008 | Barlow et al. |
| 2008/0091154 A1 | 4/2008 | Botten |
| 2008/0140057 A1 | 6/2008 | Wood et al. |
| 2008/0234641 A1 | 9/2008 | Locke et al. |
| 2008/0255808 A1 | 10/2008 | Hayter |
| 2008/0275327 A1 | 11/2008 | Faarbaek et al. |
| 2008/0278337 A1 | 11/2008 | Huang et al. |
| 2008/0300559 A1 | 12/2008 | Gustafson et al. |
| 2008/0300578 A1 | 12/2008 | Freedman |
| 2008/0306459 A1 | 12/2008 | Albrectsen |
| 2009/0012501 A1 | 1/2009 | Boehringer et al. |
| 2009/0118687 A1 | 5/2009 | Kristensen et al. |
| 2009/0167286 A1 | 7/2009 | Naylor et al. |
| 2009/0173935 A1 | 7/2009 | Cho et al. |
| 2009/0227969 A1 | 9/2009 | Jaeb et al. |
| 2009/0234916 A1 | 9/2009 | Cosentino et al. |
| 2009/0247970 A1 | 10/2009 | Keleny et al. |
| 2009/0264957 A1 | 10/2009 | Giftakis et al. |
| 2010/0010460 A1 | 1/2010 | Butler |
| 2010/0030167 A1 | 2/2010 | Thirstrup et al. |
| 2010/0072271 A1 | 3/2010 | Thorstensson |
| 2010/0106220 A1 | 4/2010 | Ecker et al. |
| 2010/0114047 A1 | 5/2010 | Song et al. |
| 2010/0191201 A1 | 7/2010 | Bach et al. |
| 2010/0271212 A1 | 10/2010 | Page |
| 2010/0311167 A1 | 12/2010 | Wood et al. |
| 2011/0034890 A1 | 2/2011 | Stroebech et al. |
| 2011/0071482 A1 | 3/2011 | Selevan |
| 2011/0077497 A1 | 3/2011 | Oster et al. |
| 2011/0130642 A1 | 6/2011 | Jaeb et al. |
| 2011/0144470 A1 | 6/2011 | Mazar et al. |
| 2011/0191044 A1 | 8/2011 | Stafford |
| 2011/0245682 A1 | 10/2011 | Robinson et al. |
| 2011/0246983 A1 | 10/2011 | Brunet et al. |
| 2011/0257496 A1 | 10/2011 | Terashima et al. |
| 2012/0013130 A1 | 1/2012 | Jung |
| 2012/0089037 A1 | 4/2012 | Bishay et al. |
| 2012/0143154 A1 | 6/2012 | Edvardsen et al. |
| 2012/0143155 A1 | 6/2012 | Edvardsen et al. |
| 2012/0258302 A1 | 10/2012 | Hunt et al. |
| 2012/0283678 A1 | 11/2012 | Nguyen-Demary et al. |
| 2012/0304767 A1 | 12/2012 | Howard et al. |
| 2012/0323086 A1 | 12/2012 | Hansen |
| 2013/0018231 A1* | 1/2013 | Hong ..................... A61F 13/42 |
| | | 600/300 |
| 2013/0030167 A1 | 1/2013 | Wang et al. |
| 2013/0030397 A1 | 1/2013 | Sabeti |
| 2013/0060213 A1 | 3/2013 | Hanuka et al. |
| 2013/0066285 A1 | 3/2013 | Locke et al. |
| 2013/0072886 A1 | 3/2013 | Schertiger et al. |
| 2013/0078912 A1 | 3/2013 | San Vicente et al. |
| 2013/0086217 A1 | 4/2013 | Price et al. |
| 2013/0102979 A1 | 4/2013 | Coulthard et al. |
| 2013/0138065 A1 | 5/2013 | Buus |
| 2013/0150769 A1 | 6/2013 | Heppe |
| 2013/0165862 A1 | 6/2013 | Griffith et al. |
| 2013/0192604 A1 | 8/2013 | Persson et al. |
| 2013/0226116 A1 | 8/2013 | Edvardsen et al. |
| 2013/0231620 A1 | 9/2013 | Thirstrup et al. |
| 2013/0254141 A1 | 9/2013 | Barda et al. |
| 2013/0267790 A1 | 10/2013 | Pfuetzner et al. |
| 2013/0303867 A1 | 11/2013 | Elfstrom et al. |
| 2013/0307570 A1 | 11/2013 | Bosaeus et al. |
| 2013/0324952 A1 | 12/2013 | Krystek et al. |
| 2013/0324955 A1 | 12/2013 | Wong et al. |
| 2013/0332085 A1 | 12/2013 | Yang et al. |
| 2014/0051946 A1 | 2/2014 | Arne et al. |
| 2014/0128815 A1 | 5/2014 | Cabiri et al. |
| 2014/0200426 A1 | 7/2014 | Taub et al. |
| 2014/0200538 A1 | 7/2014 | Euliano et al. |
| 2014/0236111 A1 | 8/2014 | Casado et al. |
| 2014/0275854 A1 | 9/2014 | Venkatraman et al. |
| 2014/0276501 A1 | 9/2014 | Cisko |
| 2014/0288381 A1 | 9/2014 | Faarbaek et al. |
| 2014/0309600 A1 | 10/2014 | Aceto et al. |
| 2014/0323909 A1 | 10/2014 | Kim |
| 2014/0327433 A1 | 11/2014 | Anway et al. |
| 2014/0336493 A1 | 11/2014 | Kulach et al. |
| 2015/0057634 A1 | 2/2015 | Mastrototaro et al. |
| 2015/0150457 A1 | 6/2015 | Wu et al. |
| 2015/0151051 A1 | 6/2015 | Tsoukalis |
| 2015/0230706 A1 | 8/2015 | Nakagawa et al. |
| 2015/0231802 A1 | 8/2015 | Quan et al. |
| 2015/0250639 A1 | 9/2015 | Thirstrup et al. |
| 2015/0257923 A1 | 9/2015 | Thirstrup et al. |
| 2015/0272495 A1 | 10/2015 | Greener |
| 2015/0328389 A1 | 11/2015 | Heppe |
| 2015/0342777 A1 | 12/2015 | Seres et al. |
| 2015/0374896 A1 | 12/2015 | Du et al. |
| 2016/0008182 A1 | 1/2016 | Prokopuk et al. |
| 2016/0015570 A1* | 1/2016 | Heinecke ............ A61F 13/0236 |
| | | 602/58 |
| 2016/0058604 A1 | 3/2016 | Wiltshire et al. |
| 2016/0084869 A1 | 3/2016 | Yuen et al. |
| 2016/0103966 A1 | 4/2016 | Mirza |
| 2016/0117062 A1 | 4/2016 | Hussam et al. |
| 2016/0158056 A1 | 6/2016 | Davis et al. |
| 2016/0158517 A1 | 6/2016 | Nebbia |
| 2016/0158969 A1 | 6/2016 | Mclane et al. |
| 2016/0166438 A1 | 6/2016 | Rovaniemi |
| 2016/0178387 A1 | 6/2016 | Yamasaki et al. |
| 2016/0198996 A1 | 7/2016 | Dullen |
| 2016/0218555 A1 | 7/2016 | Slaby et al. |
| 2016/0235581 A1 | 8/2016 | Keleny et al. |
| 2016/0235582 A1 | 8/2016 | Moavenian |
| 2016/0242654 A1 | 8/2016 | Quinlan et al. |
| 2016/0267769 A1 | 9/2016 | Rokhsaz et al. |
| 2016/0278990 A1 | 9/2016 | Chen |
| 2016/0305776 A1 | 10/2016 | Mrtensson et al. |
| 2016/0310077 A1 | 10/2016 | Hunter et al. |
| 2016/0310140 A1 | 10/2016 | Belson et al. |
| 2016/0310329 A1 | 10/2016 | Patel et al. |
| 2016/0331232 A1 | 11/2016 | Love et al. |
| 2016/0331235 A1 | 11/2016 | Nyberg et al. |
| 2016/0361015 A1 | 12/2016 | Wang et al. |
| 2017/0042614 A1 | 2/2017 | Salahieh et al. |
| 2017/0050004 A1 | 2/2017 | Tilson et al. |
| 2017/0055896 A1 | 3/2017 | Al-Ali et al. |
| 2017/0090236 A1 | 3/2017 | Yeh et al. |

(56)                    References Cited

U.S. PATENT DOCUMENTS

| | | |
|---|---|---|
| 2017/0098044 A1 | 4/2017 | Lai et al. |
| 2017/0113001 A1 | 4/2017 | Trock |
| 2017/0140103 A1 | 5/2017 | Angelides |
| 2017/0156920 A1 | 6/2017 | Hunt et al. |
| 2017/0181628 A1 | 6/2017 | Burnette et al. |
| 2017/0340474 A1 | 11/2017 | Thirstrup et al. |
| 2017/0340498 A1 | 11/2017 | Tessmer et al. |
| 2017/0348137 A1 | 12/2017 | Hvid et al. |
| 2017/0348162 A1 | 12/2017 | Arizti et al. |
| 2017/0360592 A1 | 12/2017 | Carrubba |
| 2017/0360593 A1 | 12/2017 | Cox |
| 2018/0021164 A1 | 1/2018 | Fenton |
| 2018/0021165 A1 | 1/2018 | Fenton |
| 2018/0049667 A1 | 2/2018 | Heppe |
| 2018/0055359 A1 | 3/2018 | Shamim et al. |
| 2018/0110078 A1 | 4/2018 | Mandapaka et al. |
| 2018/0136712 A1 | 5/2018 | Niikura et al. |
| 2018/0171183 A1 | 6/2018 | Sakurai et al. |
| 2018/0298240 A1 | 10/2018 | Chatterjee et al. |
| 2018/0318475 A1 | 11/2018 | Thomson et al. |
| 2019/0008439 A1 | 1/2019 | Sageder et al. |
| 2019/0133810 A1* | 5/2019 | Seres ................... A61B 5/445 |
| 2019/0133811 A1 | 5/2019 | Seres et al. |
| 2019/0133812 A1 | 5/2019 | Seres et al. |
| 2019/0142623 A1 | 5/2019 | Schoess et al. |
| 2019/0175386 A1 | 6/2019 | Monty |
| 2019/0184093 A1 | 6/2019 | Sjolund et al. |
| 2019/0192066 A1 | 6/2019 | Schoess et al. |
| 2019/0192332 A1 | 6/2019 | Hansen et al. |
| 2019/0192333 A1 | 6/2019 | Hansen et al. |
| 2019/0192334 A1 | 6/2019 | Hansen et al. |
| 2019/0240059 A1 | 8/2019 | Seres et al. |
| 2019/0247050 A1 | 8/2019 | Goldsmith |
| 2019/0252079 A1 | 8/2019 | Constantin et al. |
| 2019/0374163 A1 | 12/2019 | Faarbaek et al. |
| 2020/0000624 A1 | 1/2020 | Gibbons et al. |
| 2020/0078206 A1 | 3/2020 | Chiladakis |
| 2020/0100931 A1 | 4/2020 | Schoess et al. |
| 2020/0114535 A1 | 4/2020 | Wattam et al. |
| 2020/0188161 A1 | 6/2020 | Seres et al. |
| 2020/0246174 A1 | 8/2020 | Hansen et al. |
| 2020/0246175 A1 | 8/2020 | Hansen et al. |
| 2020/0246176 A1 | 8/2020 | Hansen et al. |
| 2020/0246177 A1 | 8/2020 | Hansen et al. |
| 2020/0276063 A1 | 9/2020 | Muñoz Herencia |
| 2020/0279368 A1 | 9/2020 | Tada et al. |
| 2020/0297244 A1 | 9/2020 | Brownhill et al. |
| 2020/0306074 A1 | 10/2020 | Speiermann et al. |
| 2020/0322793 A1 | 10/2020 | Yang |
| 2020/0330258 A1 | 10/2020 | Hansen et al. |
| 2020/0330260 A1 | 10/2020 | Hansen et al. |
| 2020/0337880 A1 | 10/2020 | Hansen et al. |
| 2020/0337881 A1 | 10/2020 | Hansen et al. |
| 2020/0337882 A1 | 10/2020 | Hansen et al. |
| 2020/0337883 A1 | 10/2020 | Hansen et al. |
| 2020/0375499 A1 | 12/2020 | Hansen et al. |
| 2020/0375782 A1 | 12/2020 | Hansen et al. |
| 2020/0375783 A1 | 12/2020 | Hansen et al. |
| 2020/0375784 A1 | 12/2020 | Hansen et al. |
| 2020/0375785 A1 | 12/2020 | Hansen et al. |
| 2020/0375786 A1 | 12/2020 | Hansen et al. |
| 2020/0375809 A1 | 12/2020 | Sullivan et al. |
| 2020/0383637 A1 | 12/2020 | Hansen et al. |
| 2020/0383818 A1 | 12/2020 | Hansen et al. |
| 2020/0383819 A1 | 12/2020 | Sletten et al. |
| 2020/0383820 A1 | 12/2020 | Hansen et al. |
| 2020/0383821 A1 | 12/2020 | Hansen et al. |
| 2020/0390587 A1 | 12/2020 | Svanegaard et al. |
| 2020/0390588 A1 | 12/2020 | Hansen et al. |
| 2020/0390589 A1 | 12/2020 | Hansen et al. |
| 2020/0395120 A1 | 12/2020 | Svanegaard et al. |
| 2020/0395610 A1 | 12/2020 | Ono et al. |
| 2020/0405228 A1 | 12/2020 | Svanegaard et al. |
| 2020/0405229 A1 | 12/2020 | Svanegaard et al. |
| 2020/0405230 A1 | 12/2020 | Svanegaard et al. |
| 2021/0000414 A1 | 1/2021 | Svanegaard et al. |
| 2021/0000633 A1 | 1/2021 | Hansen et al. |
| 2021/0000634 A1 | 1/2021 | Svanegaard et al. |
| 2021/0000635 A1 | 1/2021 | Hansen et al. |
| 2021/0000636 A1 | 1/2021 | Hansen et al. |
| 2021/0007663 A1 | 1/2021 | Svanegaard et al. |
| 2021/0007881 A1 | 1/2021 | Svanegaard et al. |
| 2021/0015653 A1 | 1/2021 | Hansen et al. |
| 2021/0015654 A1 | 1/2021 | Hansen et al. |
| 2021/0022683 A1 | 1/2021 | Faarbaek et al. |
| 2021/0038424 A1 | 2/2021 | Svanegaard et al. |
| 2021/0059603 A1 | 3/2021 | Svanegaard et al. |
| 2021/0085511 A1 | 3/2021 | Hansen et al. |
| 2021/0085512 A1 | 3/2021 | Hansen et al. |
| 2021/0100533 A1 | 4/2021 | Seres et al. |
| 2021/0128364 A1 | 5/2021 | Cole et al. |
| 2021/0145354 A1 | 5/2021 | Hunt et al. |
| 2021/0177642 A1 | 6/2021 | Andersen et al. |
| 2021/0212855 A1 | 7/2021 | Hansen et al. |
| 2021/0228194 A1 | 7/2021 | Mayberg |
| 2021/0338471 A1 | 11/2021 | Nolan et al. |
| 2021/0361464 A1 | 11/2021 | Larsen et al. |
| 2021/0361465 A1 | 11/2021 | Hansen et al. |
| 2021/0361466 A1 | 11/2021 | Hansen et al. |
| 2021/0361467 A1 | 11/2021 | Hansen et al. |
| 2021/0369197 A1 | 12/2021 | Hansen et al. |
| 2021/0369488 A1 | 12/2021 | Hansen et al. |
| 2021/0369489 A1 | 12/2021 | Hansen et al. |
| 2021/0369490 A1 | 12/2021 | Hansen et al. |
| 2021/0370217 A1 | 12/2021 | Kirschman |
| 2021/0386368 A1 | 12/2021 | Carlsson et al. |
| 2022/0000652 A1 | 1/2022 | Thirstrup et al. |
| 2022/0031227 A1 | 2/2022 | Cho et al. |
| 2022/0031495 A1 | 2/2022 | Seres et al. |
| 2022/0079802 A1 | 3/2022 | Hansen |
| 2022/0079803 A1 | 3/2022 | Windeballe et al. |
| 2022/0087851 A1 | 3/2022 | Stroebech |
| 2022/0110585 A1 | 4/2022 | Andersen |
| 2022/0117771 A1 | 4/2022 | Fearn et al. |
| 2022/0142807 A1 | 5/2022 | Tofte |
| 2022/0192860 A1 | 6/2022 | Hansen et al. |
| 2022/0241104 A1 | 8/2022 | Knoedler |
| 2022/0241105 A1 | 8/2022 | Hansen et al. |
| 2022/0265458 A1 | 8/2022 | Carlsson et al. |
| 2022/0304844 A1 | 9/2022 | Carlsson et al. |
| 2023/0059470 A1 | 2/2023 | Hansen et al. |
| 2023/0064734 A1 | 3/2023 | Hansen et al. |
| 2023/0105402 A1 | 4/2023 | Hansen et al. |
| 2023/0117727 A1 | 4/2023 | Hansen et al. |
| 2023/0118594 A1 | 4/2023 | Speiermann et al. |
| 2023/0141297 A1 | 5/2023 | Herold et al. |
| 2023/0141719 A1 | 5/2023 | Emborg et al. |
| 2023/0142141 A1 | 5/2023 | Emborg et al. |
| 2023/0145670 A1 | 5/2023 | Seres et al. |
| 2023/0146436 A1 | 5/2023 | Hansen et al. |
| 2023/0147665 A1 | 5/2023 | Hasbeck et al. |
| 2023/0190509 A1 | 6/2023 | Hansen et al. |
| 2023/0210682 A1 | 7/2023 | Hansen et al. |
| 2023/0233147 A1 | 7/2023 | Hansen et al. |
| 2023/0255811 A1 | 8/2023 | Carlsson et al. |
| 2023/0284932 A1 | 9/2023 | Hansen et al. |
| 2023/0293333 A1 | 9/2023 | Hansen et al. |
| 2023/0293335 A1 | 9/2023 | Hansen et al. |
| 2023/0301818 A1 | 9/2023 | Hansen et al. |
| 2023/0310201 A1 | 10/2023 | Hansen et al. |
| 2023/0329893 A1 | 10/2023 | Olsen et al. |
| 2023/0338005 A1 | 10/2023 | Barthe et al. |
| 2023/0372141 A1 | 11/2023 | Larsen et al. |
| 2023/0414397 A1 | 12/2023 | Hansen et al. |
| 2024/0009020 A1 | 1/2024 | Hansen et al. |
| 2024/0041635 A1 | 2/2024 | Hansen et al. |
| 2024/0180740 A1 | 6/2024 | Hansen et al. |
| 2024/0225539 A1 | 7/2024 | Svanegaard et al. |
| 2024/0261130 A1 | 8/2024 | Hansen et al. |

FOREIGN PATENT DOCUMENTS

| | | |
|---|---|---|
| CA | 3009449 C | 9/2019 |
| CA | 3002372 C | 3/2021 |

(56)                    References Cited

FOREIGN PATENT DOCUMENTS

| | | |
|---|---|---|
| CA | 2947016 C | 2/2023 |
| CN | 103269668 A | 8/2013 |
| CN | 203786580 U | 8/2014 |
| CN | 104902399 A | 9/2015 |
| CN | 104980878 A | 10/2015 |
| CN | 105588856 A | 5/2016 |
| CN | 106062546 A | 10/2016 |
| CN | 206271160 U | 6/2017 |
| CN | 206450708 U | 8/2017 |
| CN | 105615896 B | 5/2019 |
| CN | 105359167 B | 6/2019 |
| DE | 3437950 A1 | 4/1985 |
| DE | 3836590 A1 | 5/1990 |
| DE | 19953062 A1 | 5/2000 |
| DE | 19900611 C1 | 7/2000 |
| DE | 102011014321 A1 | 9/2012 |
| DE | 102011076219 A1 | 11/2012 |
| EP | 0168967 A1 | 1/1986 |
| EP | 0373782 A1 | 6/1990 |
| EP | 0416397 A1 | 3/1991 |
| EP | 0850076 B1 | 4/2005 |
| EP | 1188157 B1 | 12/2005 |
| EP | 2108345 A1 | 10/2009 |
| EP | 2489561 A2 | 8/2012 |
| EP | 2654646 A2 | 10/2013 |
| EP | 2453851 B1 | 10/2014 |
| EP | 3064179 A1 | 9/2016 |
| EP | 3213727 A1 | 9/2017 |
| GB | 2219679 A | 12/1989 |
| GB | 2225951 A | 6/1990 |
| GB | 2343628 A | 5/2000 |
| GB | 2465742 A | 6/2010 |
| GB | 2542093 A | 3/2017 |
| JP | 04-074882 A | 3/1992 |
| JP | 06-152077 A | 5/1994 |
| JP | 09-010184 A | 1/1997 |
| JP | 11-128352 A | 5/1999 |
| JP | 2000-093448 A | 4/2000 |
| JP | 2001-087299 A | 4/2001 |
| JP | 2002-055074 A | 2/2002 |
| JP | 2002-224093 A | 8/2002 |
| JP | 2005-323981 A | 11/2005 |
| JP | 2007-319561 A | 12/2007 |
| JP | 2014-033745 A | 2/2014 |
| JP | 2014-054368 A | 3/2014 |
| JP | 2014-507182 A | 3/2014 |
| JP | 2014151096 A | 8/2014 |
| KR | 10-2012-0003987 A | 1/2012 |
| NL | 1003904 C2 | 3/1998 |
| RU | 2527155 C2 | 8/2014 |
| TW | 201201783 A | 1/2012 |
| WO | 94/15562 A1 | 7/1994 |
| WO | 97/10012 A1 | 3/1997 |
| WO | 99/33037 A1 | 7/1999 |
| WO | 99/36017 A1 | 7/1999 |
| WO | 00/79497 A1 | 12/2000 |
| WO | 01/13830 A1 | 3/2001 |
| WO | 01/50996 A1 | 7/2001 |
| WO | 02/52302 A2 | 7/2002 |
| WO | 02/99765 A1 | 12/2002 |
| WO | 2004084778 A2 | 10/2004 |
| WO | 2005/038693 A1 | 4/2005 |
| WO | 2005/082271 A2 | 9/2005 |
| WO | 2006/008866 A1 | 1/2006 |
| WO | 2006/094513 A2 | 9/2006 |
| WO | 2007/000168 A1 | 1/2007 |
| WO | 2007/059774 A2 | 5/2007 |
| WO | 2007/070266 A1 | 6/2007 |
| WO | 2007/098762 A1 | 9/2007 |
| WO | 2007/133555 A2 | 11/2007 |
| WO | 2007128038 A1 | 11/2007 |
| WO | 2008/057884 A2 | 5/2008 |
| WO | 2009/006900 A1 | 1/2009 |
| WO | 2009/052496 A1 | 4/2009 |
| WO | 2009/107011 A1 | 9/2009 |
| WO | 2009/112912 A2 | 9/2009 |
| WO | 2011/003421 A1 | 1/2011 |
| WO | 2011/004165 A1 | 1/2011 |
| WO | 2011003420 A1 | 1/2011 |
| WO | 2011/061540 A1 | 5/2011 |
| WO | 2011/105701 A2 | 9/2011 |
| WO | 2011/123018 A1 | 10/2011 |
| WO | 2011/139499 A1 | 11/2011 |
| WO | 2011/161254 A2 | 12/2011 |
| WO | 2012/068386 A1 | 5/2012 |
| WO | 2012/076022 A2 | 6/2012 |
| WO | 2012/084987 A2 | 6/2012 |
| WO | 2013/013197 A1 | 1/2013 |
| WO | 2013095231 A1 | 6/2013 |
| WO | 2013164517 A1 | 11/2013 |
| WO | 2014/004207 A1 | 1/2014 |
| WO | 2014/086369 A1 | 6/2014 |
| WO | 2014116816 A1 | 7/2014 |
| WO | 2015/007284 A1 | 1/2015 |
| WO | 2015/014774 A1 | 2/2015 |
| WO | 2015/084462 A1 | 6/2015 |
| WO | 2015/094064 A1 | 6/2015 |
| WO | 2015/187366 A1 | 12/2015 |
| WO | 2015186452 A1 | 12/2015 |
| WO | 2016/132738 A1 | 8/2016 |
| WO | 2016124202 A1 | 8/2016 |
| WO | 2016/166731 A1 | 10/2016 |
| WO | 2016162038 A1 | 10/2016 |
| WO | 2016/192738 A1 | 12/2016 |
| WO | 2017/023794 A1 | 2/2017 |
| WO | 2017/062042 A1 | 4/2017 |
| WO | 2017/067558 A1 | 4/2017 |
| WO | 2017/067560 A1 | 4/2017 |
| WO | 2017/074505 A1 | 5/2017 |
| WO | 2017/088153 A1 | 6/2017 |
| WO | 2017108109 A1 | 6/2017 |
| WO | 2017/136696 A1 | 8/2017 |
| WO | 2017/190752 A1 | 11/2017 |
| WO | 2018/028756 A1 | 2/2018 |
| WO | 2019/094635 A1 | 5/2019 |
| WO | 2019/120432 A1 | 6/2019 |
| WO | 2019/161859 A1 | 8/2019 |
| WO | 2019/161860 A1 | 8/2019 |
| WO | 2019/161863 A1 | 8/2019 |
| WO | 2019/174693 A1 | 9/2019 |
| WO | 2019/174695 A1 | 9/2019 |
| WO | 2019/213623 A1 | 11/2019 |
| WO | 2020/035121 A1 | 2/2020 |

* cited by examiner

SENSOR PATCH FOR ATTACHMENT TO A BASE PLATE

BACKGROUND

Stomal output often contains body fluids and visceral contents that are aggressive to both the skin of a user and to ostomy devices, these have a detrimental effect on the efficiency and integrity of the adhesive materials that are applied to attach the ostomy device to the user's skin surface. For users in general, safe, reliable and efficient ostomy devices are evidently highly desirable.

However, a particularly major and persistent concern of a large population of ostomists continues to be failure of the base plate adhesive attaching the ostomy appliance to the user's skin surface, because such failure almost inevitably leads to embarrassing and stigmatising leakage incidents. Such incidents in turn are known from several user interviews to lead to a reduced quality-of-life feeling. Adhesive failure of the base plate adhesive can result from various reasons. Most often, a leakage incident is caused by stomal output entering between the proximal surface of the base plate and the user's skin, e.g. due to less-than-optimal attachment of the base plate to the skin arising from e.g. uneven skin surface or skin folds. This undesirable progression of stomal output "underneath" the adhesive leads to deterioration and/or weakening of the adhesive material carrying the weight and providing the seal of the ostomy appliance. Often such failure happens surprisingly fast and is only detectable for the user once the failure has already become so severe that leakage occurs, requiring immediate change of the ostomy appliance and possibly also of the user's clothes.

In other instances, the primary factor of adhesive failure is simply a question of how much time has elapsed since the base plate of the ostomy appliance was first applied to the user's skin surface. In addition to the output from the stoma itself, the peristomal skin surface continuously secretes some moisture (e.g. sweat). To mitigate this, most often adhesives of base plates for ostomy devices include hydrocolloid materials which are capable of absorbing high levels of moisture, thereby stabilizing the polymer matrix of the adhesive material and prolonging the lifetime ("wear time") of the base plate. However, eventually the adhesion capability of the base plate no longer can support the force exerted on the base plate from the load of the output collecting bag, and the appliance must be replaced.

As there can be considerable differences in the severity and/or speed by which adhesive failure and potentially leakage occur, which differences at least to some extent are correlated to various factors including those presented above, a mere indication that failure or leakage is imminent, or that it has already occurred, fails to represent a reliable and satisfactory solution to the problem of avoiding sudden embarrassing and stigmatising leakage incidents in ostomy appliances. In other words, the users of ostomy appliances could greatly benefit from an appliance solution which provides them with better guidance and options regarding how and—not least—how quickly to react to beginning failure or leakage of the adhesive of the base plate of the appliance. More generally, ostomists and health care professionals alike would welcome improvements in ostomy devices to reduce or eliminate the occurrence of sudden leakage incidents.

SUMMARY OF THE INVENTION

Disclosed is a sensor patch for attachment to a base plate for an ostomy appliance. The sensor patch comprises a distal side and a proximal side comprising at least one adhesive layer, a part of the distal side being adapted for attachment to the base plate and the proximal adhesive side adapted to adhere to the skin surface of a user.

BRIEF DESCRIPTION OF THE DRAWING

The accompanying drawings are included to provide a further understanding of embodiments and are incorporated into and a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
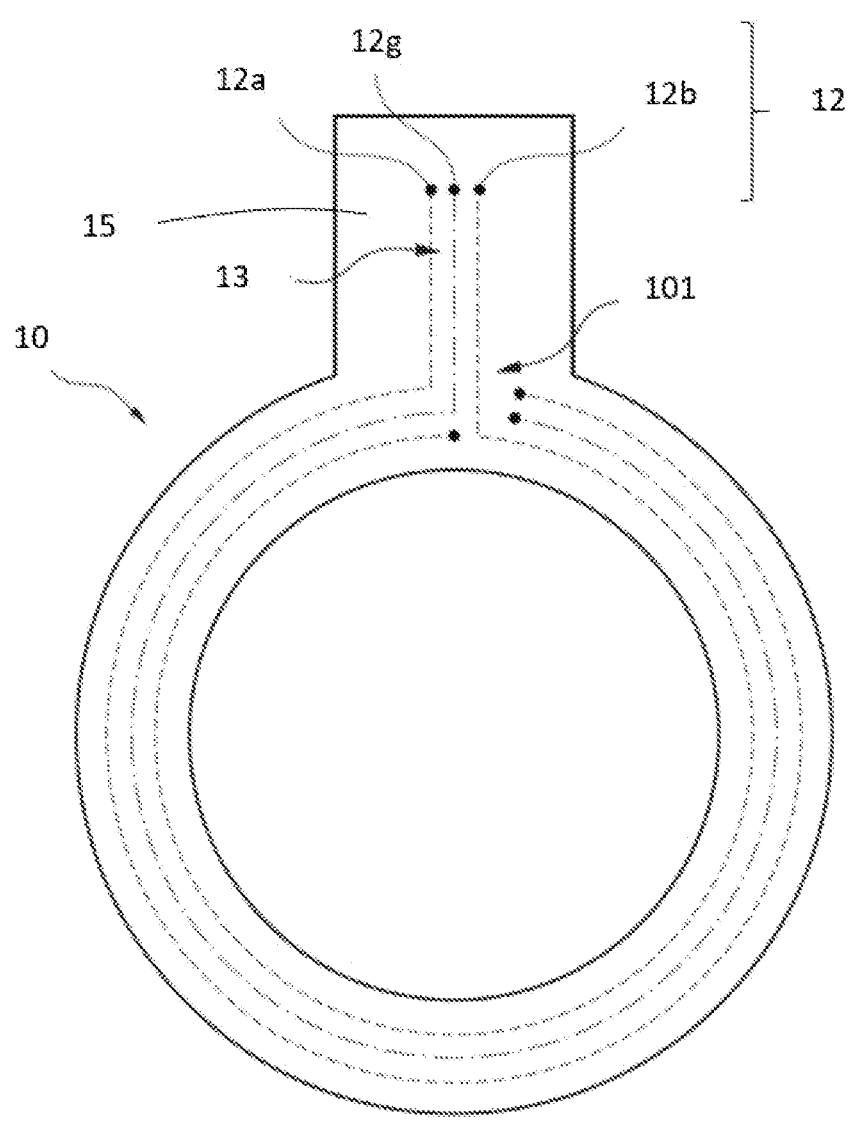
FIG. 1 illustrates a top view of an embodiment of a sensor patch.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with respect to the orientation of the Figure(s) being described. Because components of embodiments can be positioned in a number of different orientations, the directional terminology is used for purposes of illustration and is in no way limiting. It is to be understood that other embodiments may be utilized, and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

Throughout this disclosure, the words "stoma" and "ostomy" are used to denote a surgically created opening bypassing the intestines or urinary tract system of a person. The words are used interchangeably, and no differentiated meaning is intended. The same applies for any words or phrases derived from these, e.g. "stomal", "ostomies" etc.

Also, the solid and liquid wastes emanating from the stoma may be referred to as both stomal "output," "waste (s)," and "fluids" interchangeably. A subject having undergone ostomy surgery may be referred to as "ostomist" or "ostomate" moreover, also as "patient" or "user". However, in some cases "user" may also relate or refer to a health care professional (HCP), such as a surgeon or an ostomy care nurse or others. In those cases, it will either be explicitly stated, or be implicit from the context that the "user" is not the "patient" him- or herself.

In the following, whenever referring to proximal side of a device or part of a device, the referral is to the skin-facing side, when the ostomy appliance is worn by a user. Likewise, whenever referring to the distal side of a device or part of a device, the referral is to the side facing away from the skin, when the ostomy appliance is worn by a user. In other words, the proximal side is the side closest to the user, when the appliance is fitted on a user and the distal side is the opposite side the side furthest away from the user in use.

The axial direction is defined as the direction of the stoma, when the appliance is worn by a user. Thus, the axial direction is generally perpendicular to the skin or abdominal surface of the user.

The radial direction is defined as transverse to the axial direction that is transversely to the direction of the stoma, i.e. "across" the distal/proximal surface of the base plate. In some sentences, the words "inner" and "outer" may be used. These qualifiers should generally be perceived with respect to the radial direction, such that a reference to an "outer" element means that the element is farther away from a centre portion of the ostomy appliance than an element referenced as "inner". In addition, "innermost" should be interpreted as the portion of a component forming a centre of the component and/or being adjacent to the centre of the component. In analogy, "outermost" should be interpreted as a portion of a component forming an outer edge or outer contour of a component and/or being adjacent to that outer edge or outer contour.

The use of the word "substantially" as a qualifier to certain features or effects in this disclosure is intended to simply mean that any deviations are within tolerances that would normally be expected by the skilled person in the relevant field.

The use of the word "generally" as a qualifier to certain features or effects in this disclosure is intended to simply mean—for a structural feature: that a majority or major portion of such feature exhibits the characteristic in question, and—for a functional feature or an effect: that a majority of outcomes involving the characteristic provide the effect, but that exceptionally outcomes do no provide the effect.

The use of the word "essentially" as a qualifier to certain structural and functional features or effects in this disclosure is used for emphasizing what is the most important focus of something or fact about something (i.e. a feature may have or fulfil a variety of effects, but when the disclosure discusses one effect as being "essentially" provided, this is the focus and the most important effect in relation to the disclosure).

Throughout the disclosure, the use of the terms "first", "second", "third", "fourth", "primary", "secondary", "tertiary" etc. does not imply any particular order or importance but are included merely to identify individual elements. Furthermore, the labelling of a first element does not imply the presence of a second element and vice versa.

Disclosed is a sensor patch for attachment to a base plate for an ostomy appliance, such as to facilitate detection of moisture propagation in the adhesive material provided for attaching the base plate to the skin surface of a user as well as detection of increased risk of leakage. For example, the sensor patch may allow electronic measurements of performance of the base plate and/or to facilitate detection of increasing risks of leakage and/or to facilitate detection of decreasing adherence of the base plate to the skin of the user.

The ostomy appliance comprises a base plate and an ostomy pouch (also referred to as an ostomy bag). The ostomy appliance may be a colostomy appliance, an ileostomy appliance or a urostomy appliance. The ostomy appliance may be a two-part ostomy appliance, i.e. the base plate and the ostomy pouch may be releasably coupled e.g. with a mechanical and/or an adhesive coupling, e.g. to allow that a plurality of ostomy pouches can be utilized (exchanged) with one base plate. For example, the base plate may comprise a coupling ring for coupling an ostomy pouch to the base plate. Further, a two-part ostomy appliance may facilitate correct application of the base plate to skin, e.g. to an improved user sight of the stomal region. Alternatively, the ostomy appliance may be a one-part ostomy appliance, i.e. the base plate and the ostomy pouch may be fixedly attached to each other. The base plate is configured for coupling to a user's stoma and/or skin surrounding the stoma, such as a peristomal skin area.

The base plate may comprise a first adhesive layer, i.e. a first layer of an adhesive material. During use, a proximal surface of the first adhesive layer adheres to the user's skin in the peristomal area and/or to additional seals, such as sealing paste, sealing tape and/or sealing ring. The first adhesive layer may be made of a first composition. The first composition may comprise one or more polyisobutenes and/or styrene-isoprene-styrene. The first composition may comprise one or more hydrocolloids. The first composition may comprise one or more water soluble or water swellable hydrocolloids. The first composition may be a pressure sensitive adhesive composition suitable for medical purposes comprising a rubbery elastomeric base and one or more water soluble or water swellable hydrocolloids. The first adhesive layer may comprise a distal surface and a proximal surface. The proximal surface of the first adhesive layer may be configured to adhere to the user's skin. The distal surface of the first adhesive layer may be configured to face away from the skin of the user.

The first adhesive layer may form the adhesive surface of the base plate adapted for attachment of the base plate to the skin surface of the user. The first adhesive layer may form part of the adhesive surface of the base plate adapted for attachment of the base plate to the skin surface of the user.

The base plate may comprise a second adhesive layer, i.e. a second layer of an adhesive material, also denoted rim adhesive layer. The second adhesive layer may be of a different adhesive material than the first adhesive layer. The second adhesive layer may be made of a second composition. The second composition may comprise one or more polyisobutenes and/or styrene-isoprene-styrene. The second composition may comprise one or more hydrocolloids. The second composition may comprise one or more water soluble or water swellable hydrocolloids. The second composition may be a pressure sensitive adhesive composition suitable for medical purposes comprising a rubbery elastomeric base and one or more water soluble or water swellable hydrocolloids. The second adhesive layer may comprise a distal surface and a proximal surface. The proximal surface of the second adhesive layer may be configured to adhere to the user's skin, e.g. at least at a rim portion of the second adhesive layer. The distal surface of the second adhesive layer may be configured to face away from the skin of the user. The second adhesive layer may be covering a larger area than the first adhesive layer, e.g.

such that the proximal surface of the second adhesive layer forms an adhesive rim surrounding the first adhesive layer.

Generally, the sensor patch may comprise at least a first and second adhesive layer, which may be made of same type of compositions as the at least first and second adhesive layers of the base plate as described above.

The sensor patch is adapted for attachment to the base plate. For example, the sensor patch may be configured to be positioned between the skin of the user and the proximal side of the base plate. For example, the sensor patch may be adapted for attachment to the first adhesive layer of the base plate. For example, a distal side of the sensor patch may be configured to be facing the proximal surface of the first adhesive layer of the base plate. For example, the sensor patch, such as a distal side of the sensor patch may be configured to adhere to the proximal surface of first adhesive layer of the base plate.

The sensor patch may comprise a stomal opening and/or the sensor patch may be adapted to form a stomal opening. Each layer of the sensor patch, as described below, may comprise stomal openings and/or be adapted to form a stomal opening for collectively forming the stomal opening of the sensor patch. The stomal opening of the sensor patch may be configured to be aligned with the stomal opening of the base plate, such as to collectively form the stomal opening of the combined base plate and sensor patch. The size and/or shape of the stomal opening of the sensor patch may be adjusted by the user or nurse before application of the sensor patch to accommodate the user's stoma. The size and/or shape of the stomal opening of the sensor patch may be adjusted together with adjustment of the stomal opening of the base plate, e.g. after the sensor patch has been attached to the base plate. The stomal opening(s) may have a centre point.

The sensor patch may comprise a sensor assembly. The sensor assembly may form a sensor assembly layer. The sensor assembly may have a distal side and a proximal side. The sensor patch may be configured to be positioned on the base plate such that the distal surface of the sensor assembly is coupled to the proximal adhesive surface of the base plate.

The sensor assembly may comprise a plurality of electrodes. The plurality of electrodes may include a first electrode and a second electrode for forming a first sensor. The plurality of electrodes may include a third electrode, a fourth electrode, a fifth electrode and/or a sixth electrode. The first electrode may be a common ground electrode. For example, a second sensor may be formed by the first electrode and the third electrode, a third sensor may be formed by the first electrode and the fourth electrode, a fourth electrode may be formed by the first electrode and the fifth electrode, and/or a fifth electrode may be formed by the first electrode and the sixth electrode. Each electrode may have respective connection parts for connecting the electrodes to respective terminal elements of a monitor device.

The plurality of electrodes is electrically conductive and may comprise one or more of metallic (e.g. silver, copper, gold, titanium, aluminium, stainless steel), ceramic (e.g. ITO), polymeric (e.g. PEDOT, PANI, PPy), and carbonaceous (e.g. carbon black, carbon nanotube, carbon fibre, graphene, graphite) materials.

The plurality of electrodes may form loops and/or open loops. Open loop electrode(s) enable(s) electrode arrangement in few or a single electrode layer.

The sensor assembly may comprise a support layer, e.g. with a proximal surface and a distal surface. The plurality of electrodes may be provided, such as formed, on the proximal surface of the support layer, e.g. the plurality of electrodes may be positioned on the proximal surface of the support layer.

The sensor assembly may comprise a masking element, e.g. with a proximal surface and a distal surface. The masking element may be configured to electrically insulate at least parts of the plurality of electrodes from proximal layers, such as a first adhesive sensor layer. The masking element may cover or overlap parts of the plurality electrodes, e.g.

when seen in the axial direction.

The sensor patch may comprise a first adhesive sensor layer, e.g. with a proximal side and a distal side. The first adhesive sensor layer may be arranged on a proximal side of the sensor assembly. The first adhesive sensor layer, such as the proximal side of the first adhesive sensor layer, may form the proximal side of the sensor patch. The proximal side of the first adhesive sensor layer may be configured to adhere to the user's skin. Thus, after being applied to the base plate, the combined base plate and sensor patch may form an adhesive proximal surface configured to be applied to the skin surface of the user. The first adhesive sensor layer may be made of a first adhesive sensor material, such as the first composition, the second composition or a third composition. The third composition may comprise one or more polyisobutenes and/or styrene-isoprene-styrene. The third composition may comprise one or more hydrocolloids. The third composition may comprise one or more water soluble or water swellable hydrocolloids. The third composition may be a pressure sensitive adhesive composition suitable for medical purposes comprising a rubbery elastomeric base and one or more water soluble or water swellable hydrocolloids.

The sensor patch is adapted to form a stomal opening with a centre point. The stomal opening is configured to allow passage of output through the stomal opening and into an ostomy pouch attached to the base plate.

As the sensor patch may allow electronic measurements of performance of the base plate and/or to facilitate detection of increasing risks of leakage and/or to facilitate detection of decreasing adherence of the base plate to the skin of the user, it is important that the sensor patch perform its function and do deliver reliable detections. It is desirable to provide a sensor patch that is comfortable to use and to provide a sensor patch that may reduce the risk of rupture which evidently will lead to false measurements and non-detected undesired leakage.

Embodiments relates to a sensor patch for attachment to a base plate for an ostomy appliance. The sensor patch comprises a distal side and a proximal side comprising at least one adhesive layer, a part of the distal side being adapted for attachment to the base plate and the proximal adhesive side adapted to adhere to the skin surface of a user, the sensor patch comprises two or more electrodes and a monitor interface for forming a connection to a monitor device, the sensor patch comprises a central portion and a neck portion, the electrodes extend from the central portion to the neck portion, the neck portion comprises a flexible element being adapted to allowing the central portion and the neck portion to be flexibly movable relative to each other.

Hereby, a sensor patch following the movements of the user is provided, thus the sensor patch is more comfortable to use. Moreover, the mechanical stresses are more evenly distributed, thus the risk of rupture of the sensor patch is reduced.

The flexible element allows the central portion and the neck portion of the sensor patch to move relative to each other following the movement of the skin of a user, and thereby provide a more comfortable sensor patch. The neck portion of the sensor patch is affected by mechanical stresses when the sensor patch is adhered to the base plate and due to movement of the user. The sensor patch may distribute mechanical stresses in the transition zone at the rim of the base plate more evenly and reduces the risk of rupture in the neck portion of the sensor patch.

Additionally, by distributing the mechanical stress more evenly, the sensor patch feels more comfortable on the sensitive skin surrounding the stoma.

The skin of the abdomen of a user of an ostomy appliance may be sensitive and the provision of a flexible neck portion will reduce the amount of undesirable and uncomfortable stretching of the peristomal skin.

In embodiments, the flexible element may be positioned juxtaposed the central portion of the sensor patch. Mechanical stresses in the transition zone between the central portion and the neck portion may be more evenly distributed and the risk of rupture in the neck portion of the sensor patch is reduced.

In embodiments, the flexible element may comprise one or more elongated through-going apertures.

In embodiments, the flexible element may comprise one or more elongated through-going slits.

In embodiments, the flexible element may comprise one or more indents, the indents extend inwards from the periphery of the neck portion towards a centre axis (C.A) extending radially from a centre point of the central portion to the monitor interface at the neck portion.

Generally, the use of the term "centre axis" is meant in this disclosure as a centre axis extending radially from an innermost centre point of the central portion to the position of the monitor interface at the neck portion. The centre axis (C.A) is illustrated in some of the figures by a dotted line.

In embodiments, the neck portion may be symmetric shaped along the centre axis. The flexible element and the sensor patch may be more flexible and stretchable particularly in radial direction in relation to the centre axis (C.A).

In embodiments, at least some of the one or more elongated through-going apertures, the one or more elongated through-going slits and/or the one or more indents may extend perpendicularly to the centre axis.

In embodiments, at least some of the one or more elongated through-going apertures, the one or more elongated through-going slits and/or the one or more indents are arranged in parallel rows, every other row may be offset with respect to intermediate rows as to form an accordion-shaped or zig zag-like pattern. The flexible element and the sensor patch may be more flexible and stretchable and allow the central portion and the neck portion to be flexibly movable relative to each other.

In embodiments, at least some of the one or more elongated through-going apertures, the one or more elongated through-going slits and/or the one or more indents may be arranged symmetrically along the centre axis.

In embodiments, at least some of the one or more elongated through-going apertures, the one or more elongated through-going slits and/or the one or more indents may comprise rounded edges. Hereby, risk of cracks in the top film is reduced and the fracture properties are improved.

In embodiments, the proximal side of the sensor patch may comprise at least a first and a second adhesive layer. Hereby, a further variation in construction of a sensor patch is provided.

In embodiments, the at least first and the second adhesive layers may be positioned adjacent each other in radial direction, the first adhesive layer may cover at least part of the central portion and the second adhesive layer covers at least part of the neck portion.

In embodiments, the at least first and second adhesive layers are made of compositions having different elastic properties, the second adhesive layer covering the flexible element of the neck portion is more flexible and/or stretchable than the first adhesive layer covering at least part of the central portion. Hereby, the adhesive layer of the flexible element allows the sensor patch to be stretched more without reaching plastic deformation, and thereby the risk of rupture of the sensor patch at the neck portion is reduced, especially at the periphery of the neck portion adjacent the overlapping parts of the sensor patch adhered to the base plate.

In embodiments, the second adhesive layer extends in radially direction towards the innermost portion of the sensor patch configured for providing an overlap of the second adhesive layer and the outer rim of the base plate when adhered together. Hereby, the mechanical stresses occurring at the periphery of the sensor patch is reduced, and rupture of the neck portion is reduced.

In embodiments, the outer contour of the sensor patch comprises an oval or pear-shape, the neck portion being narrower than the central portion. Provision of a neck for a sensor patch having a design reducing mechanical stress of the neck of sensor patch and sensor elements.

In embodiments, the neck portion may have a length along the centre axis from the centre point of the central portion to the interface coupling of 40-110 mm, such as 60-90 mm, such as 70 mm. Thereby a universal sensor patch for use with a base plate is provided. This allows the user to couple a monitor device to the interface coupling outside but still at the proximity of the outer periphery of the base plate.

In embodiments, at least part of the electrodes comprises a z-shaped layout or similar pattern to form flexible electrodes. Allowing the sensor patch to be stretched without breaking or destroy the sensibility of the electrodes.

Embodiments, and features of the various exemplary embodiments described in this application, may be combined with each other ("mixed and matched"), unless specifically noted otherwise.

DETAILED DESCRIPTION OF THE DRAWINGS

FIG. 1-7 show an embodiment of a sensor patch.

Figure 2:
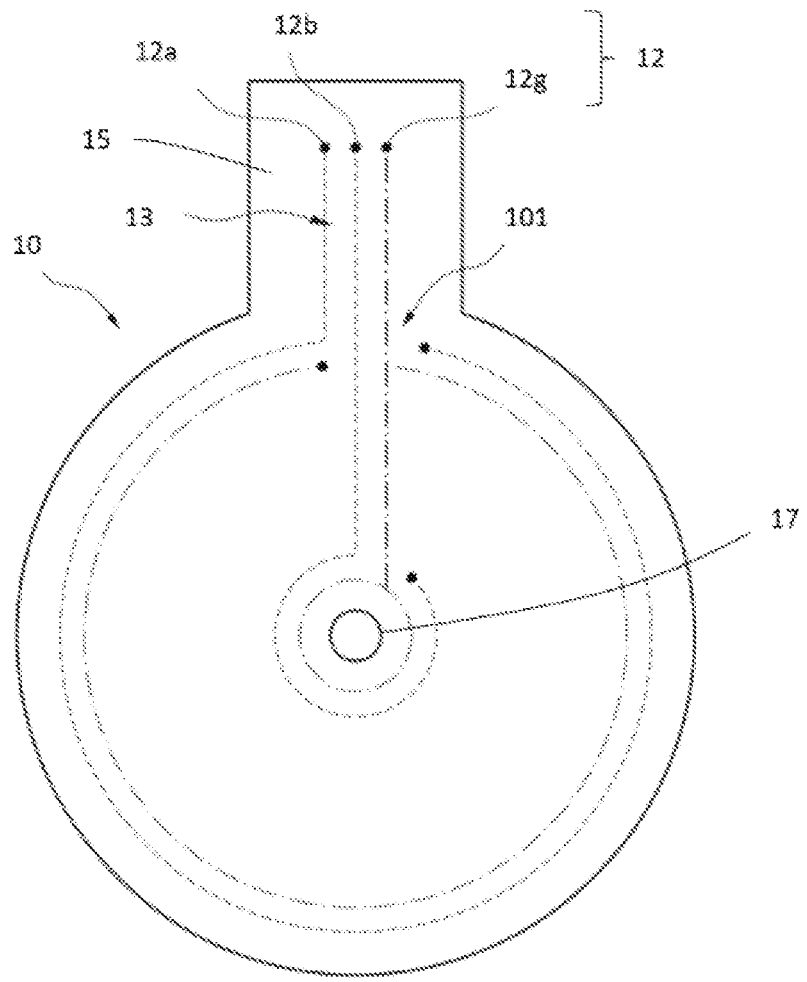
FIG. 2 illustrates an embodiment of a sensor patch.

FIG. 1 and FIG. 2 illustrate a top view of a sensor patch 10 comprising a first electrode 12a, a second electrode 12b and a ground electrode 12g arranged in a spatial layout 101. The electrodes 12a, 12b are provided on a distal surface of an adhesive layer 15.

The distal surface of the sensor patch is adapted for attachment to an adhesive surface of a baseplate (not shown in the figures), whereby the electrodes 12a, 12b, 12g become layered between the adhesive layer 15 and the baseplate. The spatial layout 101 is shown to resemble a majority of a ring and comprises a monitor interface 13. The monitor interface 13 comprises contact points for establishing an electrical connection between the electrodes 12a, 12b, 12g and a monitor device capable of controlling and assessing a current in the electrodes. The monitor interface 13 is provided in a neck portion 185 extending radially away from a centre point 4 of the sensor patch 10. The neck portion 185 is configured with a length sufficient to extend beyond the extension of a baseplate onto which the sensor patch is to be attached.

The electrodes 12 (12a,12b,12g) form one or more sensors. The sensor patch 10 comprises a layout of three electrodes; a first electrode 12a, a second electrode 12b, and a ground electrode 12g. The first 12a and the second electrode 12b are live. The ground electrode 12g forms the ground for the live first 12a and second electrodes 12b. Thereby, two sensors are formed. The first sensor can be formed between the first electrode 12a and the ground electrode 12g, and a second sensor can be formed between the second electrode 12b and the ground electrode 12g. The one or more sensors enable that changes in relevant electrical quantities, e.g. resistance, can be monitored. Thereby, the sensor patch 10 comprises sensing abilities.

Generally, the sensor patch is adapted for attachment to a baseplate for monitoring the presence or liquid in an interface between the skin surface of a user and the baseplate. In addition, the sensor patch can be adapted for assessing the amount of moisture absorbed in the adhesive layer, whereby the state or health of the adhesive of the baseplate can be assessed. The state or health of the adhesive of the baseplate may be indicative of erosion and can be used for predicting imminent risk of leakage and/or detachment of the baseplate.

FIG. 2 illustrates a sensor patch 10 comprising three electrodes in an alternative spatial layout 101 to the spatial layout illustrated in FIG. 1. The sensor patch comprises a first electrode 12a, a second electrode 12b, and a ground electrode 12g. The first 12a and the second electrode 12b are live. The electrodes 12a,12b,12g and a monitor interface 13 are configured for forming a connection to a monitor device. The ground electrode 12g forms the ground for the live first 12a and second electrodes 12b. Thereby, two sensors are formed. A first sensor can be formed between the first electrode 12a and the ground electrode 12g, and a second sensor can be formed between the second electrode 12b and the ground electrode 12g.

In FIG. 2 the electrodes 12,12a,12b,12g extend in a spatial layout 101 having electrodes at the innermost rim of the sensor patch at the stomal opening 17.

Figure 3:
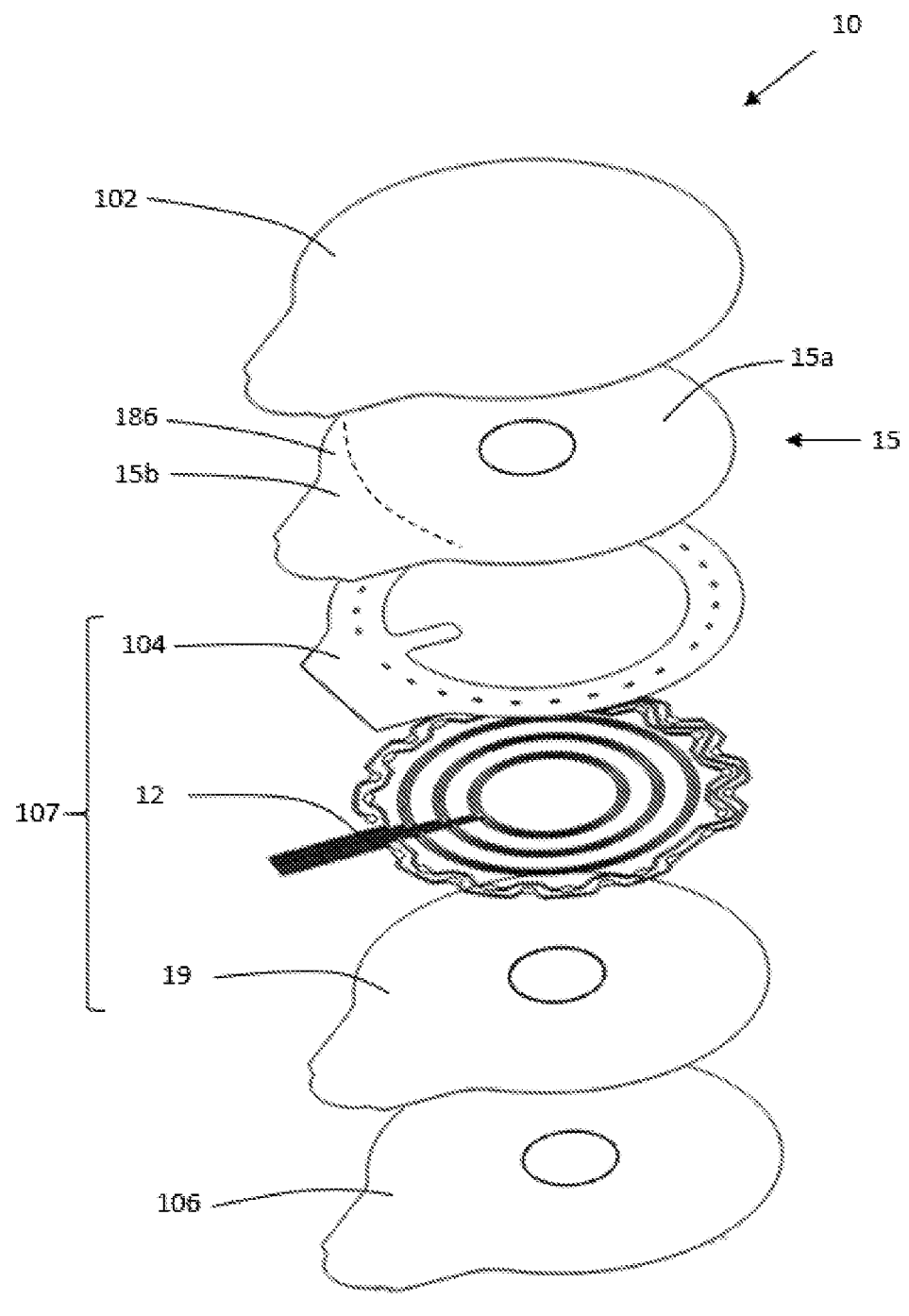
FIG. 3 is an exploded view of a sensor plate.

FIG. 3 illustrates an exploded view of a sensor patch 10. The sensor patch 10 comprises a sensor assembly 107 comprising a support layer 19 with electrodes 12 formed on a proximal surface of the support layer.

The sensor assembly 107 comprises a masking element 104, e.g. with a proximal surface and a distal surface. The masking element 104 may be configured to electrically insulate at least parts of the plurality of electrodes 12 from proximal layers, such as a first adhesive sensor layer 15. The masking element covers or overlaps parts of the plurality electrodes, e.g. when seen in the axial direction.

The sensor patch 10 comprises a first adhesive layer 15. The first adhesive layer is arranged on a proximal side of the sensor assembly 107. The first adhesive layer 15 forms the proximal side of the sensor patch. The proximal side of the first adhesive sensor layer is configured to adhere to the user's skin. The adhesive layer of the sensor patch may be provided with a release liner 102 and the distal side may be provided with a top film on the distal side.

In embodiments, the proximal side of the sensor patch comprises at least a first and second adhesive layer 15a,15b. This is illustrated by a dotted line in FIG. 3. The two adhesive layers 15a,15b are positioned adjacent to each other in radial direction, a first adhesive layer 15a covering at least part of the central portion and a second adhesive layer 15b covering the neck portion 185. The neck portion extends further than the outer rim of the base plate when the sensor patch is applied to such base plate, thereby leaving a part of the neck portion unattached to the base plate. The flexible element may be positioned at the neck portion 185 adjacent or overlapping with the outer rim of the base plate in radial direction.

Generally, the central portion 180 comprises a first adhesive 15a and the neck portion comprises a second adhesive 15b. In embodiments, the first adhesive and the second adhesive are the same type of adhesive. In embodiments, the first adhesive and the second adhesive may have different properties. For example, the adhesives may differ with respect to adhesive tack and/or softness.

Generally, the sensor patch may comprise at least a first and a second adhesive layers made by one or more compositions comprising one or more polyisobutenes and/or styrene-isoprene-styrene. The one or more composition may comprise one or more hydrocolloids. The one or more composition may comprise one or more water soluble or water swellable hydrocolloids. The one or more composition may be a pressure sensitive adhesive composition suitable for medical purposes comprising a rubbery elastomeric base and one or more water soluble or water swellable hydrocolloids.

In generally, the second adhesive layer 15b may cover at least part of the neck portion which may be more flexible and stretchable than the adhesive layer 15a covering the central portion. The two adhesive layers are made of compositions comprising different properties relating to flexibility, allowing the adhesive layer of the flexible element to be stretched in radially direction without plastic deformation.

In embodiments, the second flexible adhesive layer covering the neck portion extends in radially direction towards the innermost portion of the sensor patch configured for an overlap of the flexible adhesive layer and the outer periphery of the base plate.

Generally, the at least first and second adhesive layers may have a substantially uniform thickness. The first adhesive layer may have a thickness in the range from 0.1 mm to 1.5 mm, for example in the range from 0.2 mm to 1.2 mm.

Figure 4:
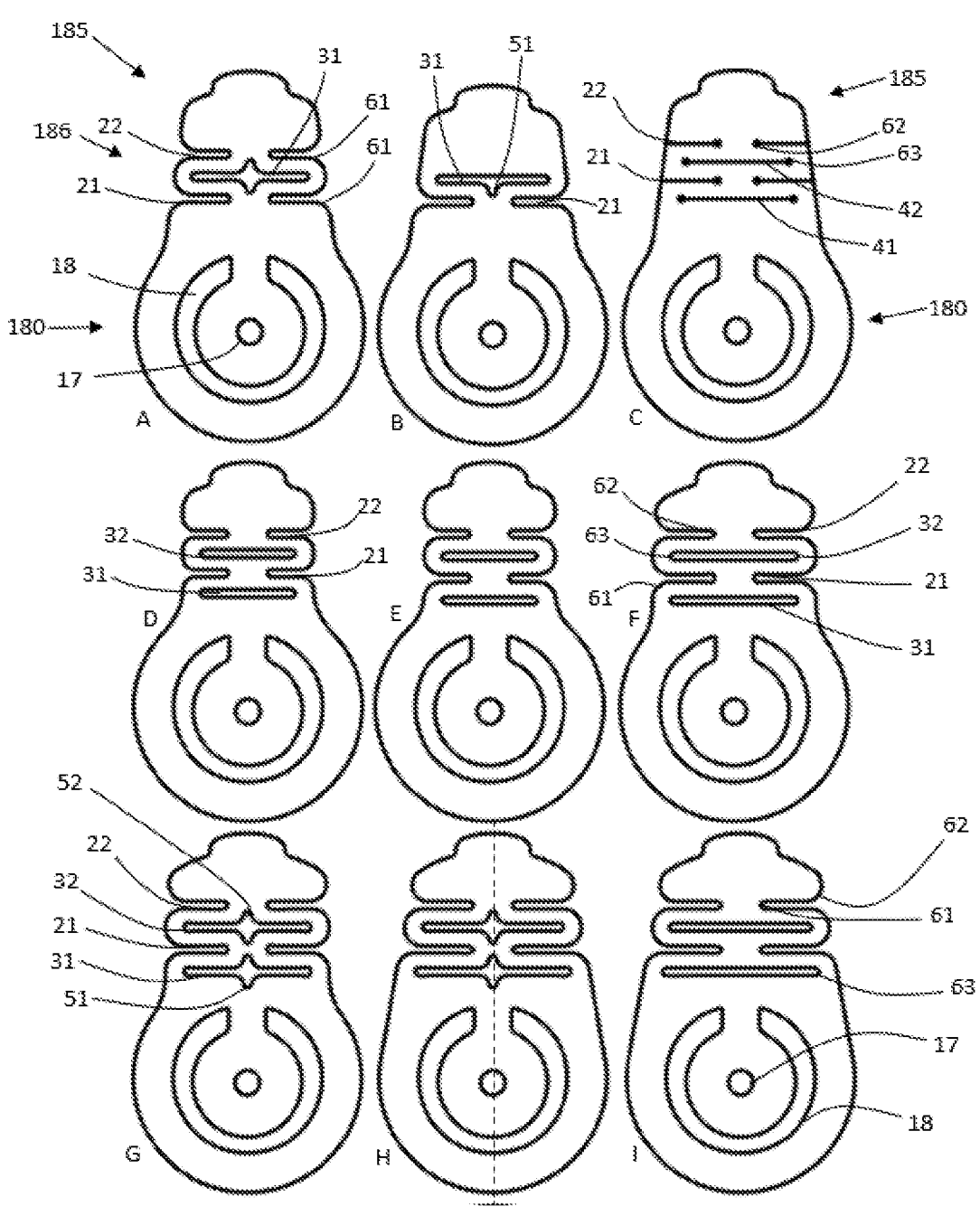
FIG. 4 illustrates embodiments (A to I) of a sensor patch.
Figure 5:
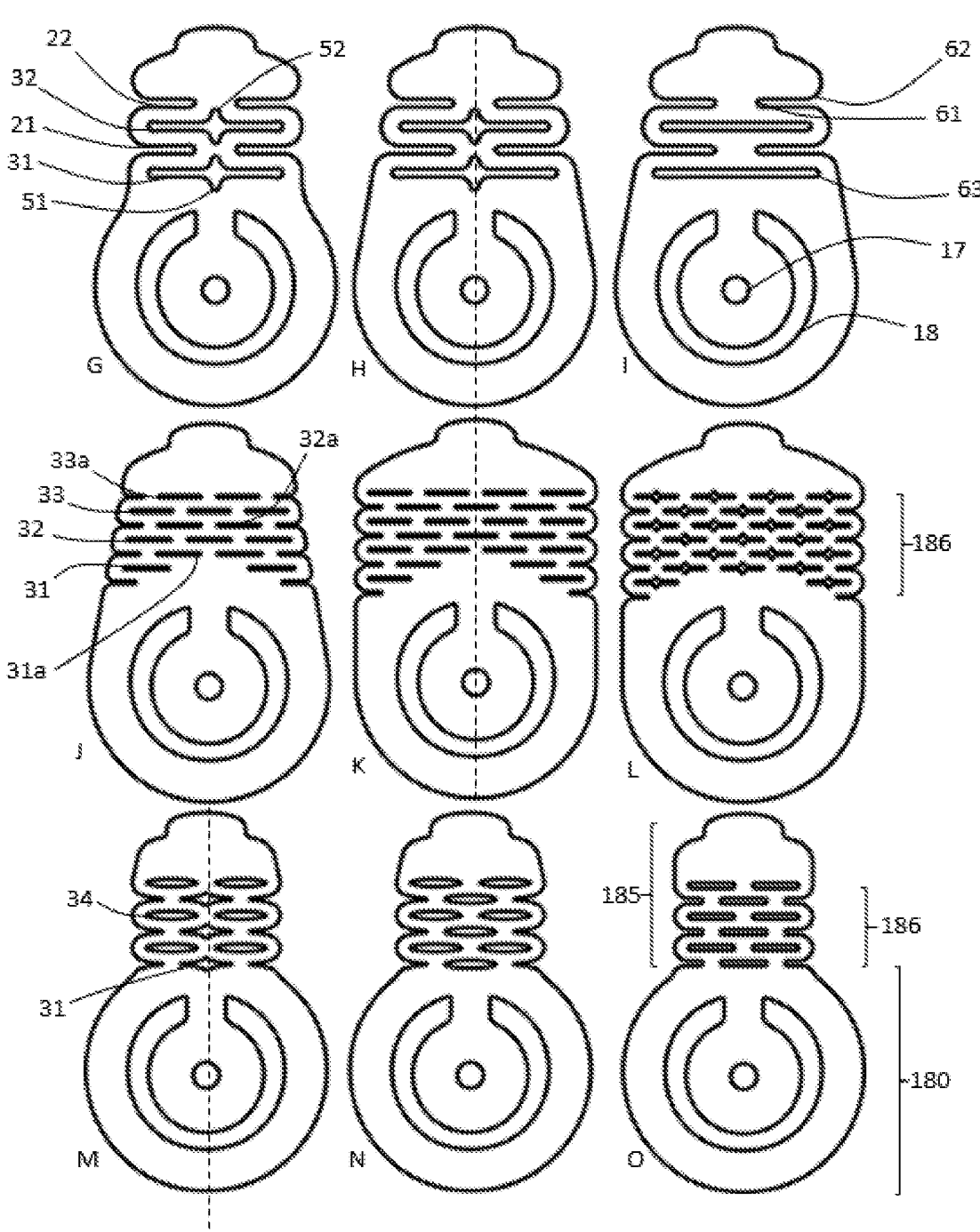
FIG. 5 illustrates embodiments (J to O) of a sensor patch.

FIG. 4 and FIG. 5 illustrate embodiments of a sensor patch. Embodiments A to I is illustrated in FIG. 4 and embodiments J to O are illustrated in FIG. 5.

FIG. 4-A illustrates a sensor patch comprising a central portion 180 and a neck portion 185 and a flexible element 186 positioned at the neck portion 185 adjacent the central portion 180. The central portion comprises a stomal opening 17 and a through-going opening 18 partly encircling the stomal opening 17.

The flexible element 186 comprises a first row of two indents 21 and a second row of two indents 22. A cross-shaped elongated through-going aperture 31 is positioned between the first and second row of indents 21,22. The elongated through-going aperture 31 and the four indents 21,22 extend in parallel across the neck portion perpendicular to the centre axis extending radially from a centre point 4 of the central portion to the position of the monitor interface at the neck portion.

FIG. 4-B illustrates a flexible element 186 comprising a single row of two indents 21 and an elongated through-going aperture 31, which comprises an indentation 51 extending across the elongated through-going aperture 31 forming a T-shaped elongated through-going aperture.

FIG. 4-C illustrates two rows of two indents 21,22 and two elongated through-going slits 41,42 comprising rounded ends 62, 63. The first innermost positioned row is one elongated through-going slit 41.

FIG. 4-D illustrates a flexible element 186 comprising two elongated through-going slits 31,32 arranged in a first set of two parallel rows. The flexible element 186 comprises four indents 21,22. The indents 21,22 extend inwards from the periphery of the neck portion towards the centre axis. The indents extend perpendicular to the centre axis and are arranged in a second set of two parallel rows. The first set and second set of rows are positioned in parallel intermediate each other. Every other row being offset with respect to intermediate rows as to form an accordion-shaped or zig zag-shaped pattern.

FIG. 4-F illustrates a similar sensor patch as illustrated in FIG. 4-D. The width of the neck portion is larger in the embodiment illustrated in FIG. 4-F, thus the indents and the through-going slits comprise a longer length as to form uniformed sizes of tracks for the electrodes extending through the flexible element from the central portion 180 to the monitor interface (not shown).

FIG. 4-G illustrates an embodiment of the sensor patch which comprises a flexible element 186 comprising a first set of rows, each row comprising two indents 21,22 and a second set of rows, each row comprises an elongated through-going aperture 31. The elongated through-going aperture 31 comprises two indentations 51,52 across the midpoint, thereby the two elongated through-going apertures 31 comprise a cross-shape.

The two elongated through-going apertures 31 and the four indents 21,22 extend in parallel across the neck portion perpendicular to the centre axis. The first set of rows and the second set of rows are being offset with respect to intermediate rows as to form an accordion-shaped or zig zag-shaped pattern, and the two elongated through-going apertures 31,32 and the four elongated indents are arranged symmetrically along the centre axis, such that the centre axis forms an axis of symmetry.

The outer contour of the sensor patch comprises a pear-shape. The embodiment illustrated in FIG. 4-H comprises a similar shaped flexible element as the embodiment illustrated in FIG. 4-G, however the two elongated through-going apertures 31,32 and the four elongated indents are slightly longer and the neck portion slightly wider.

The embodiment illustrated in FIG. 4-H and 4-I comprises similar shape, however the indentations 51 from the embodiment illustrated in FIG. 4-G are removed. Hereby, it is apparent that there are great possibilities of variations for how to shape a sensor patch and the flexible portion.

The embodiments of a sensor patch illustrated in FIG. 5 comprise a plurality of parallel staggered rows and different widths of the neck portion.

In FIG. 5-J a first set of parallel elongated through-going slits, 31,32,33, and a second set of parallel elongated through-going slits 31a,32a,33a and indents 21,22,23,24 are positioned off set in a direction perpendicular to the centre axis in between the first set of parallel elongated through-going slits, 31,32,33.

In FIG. 5-K a similar shaped sensor patch is illustrated. The neck portion comprises a width equal to the central portion, thus the number of slits in each row is increased. Some rows comprise a line of four consecutive through-going slits.

Additionally, some of the rows toward the inner most part of the sensor patch are omitted. The size of the flexible element 186 may vary and the part of the flexible element abutting the central portion may comprise an inner curved shape as illustrated in FIG. 5-L.

The shape of the elongated through-going apertures may vary as well. The shape may be formed like an oval-shape or a diamond-shape as illustrated in FIG. 5-M.

The embodiment in FIG. 5-O illustrates the extension of the central portion 180, the neck portion 185 and the flexible portion 186. The flexible portion being positioned abutting the central portion 180 forming a transition zone between the central portion 180 and the neck portion 185.

The outer contour of the sensor patch may comprise an oval or pear-shape, the neck portion being narrower than the central portion.

The outer contour of the sensor patch illustrated in FIG. 4-K and 4-L comprises an oval shape, where the neck portion comprises a width similar to the central portion. In other embodiments the outer contour comprises a pear-shape, where the neck portion has a narrower width than the central portion across the centre axis.

Figure 6:
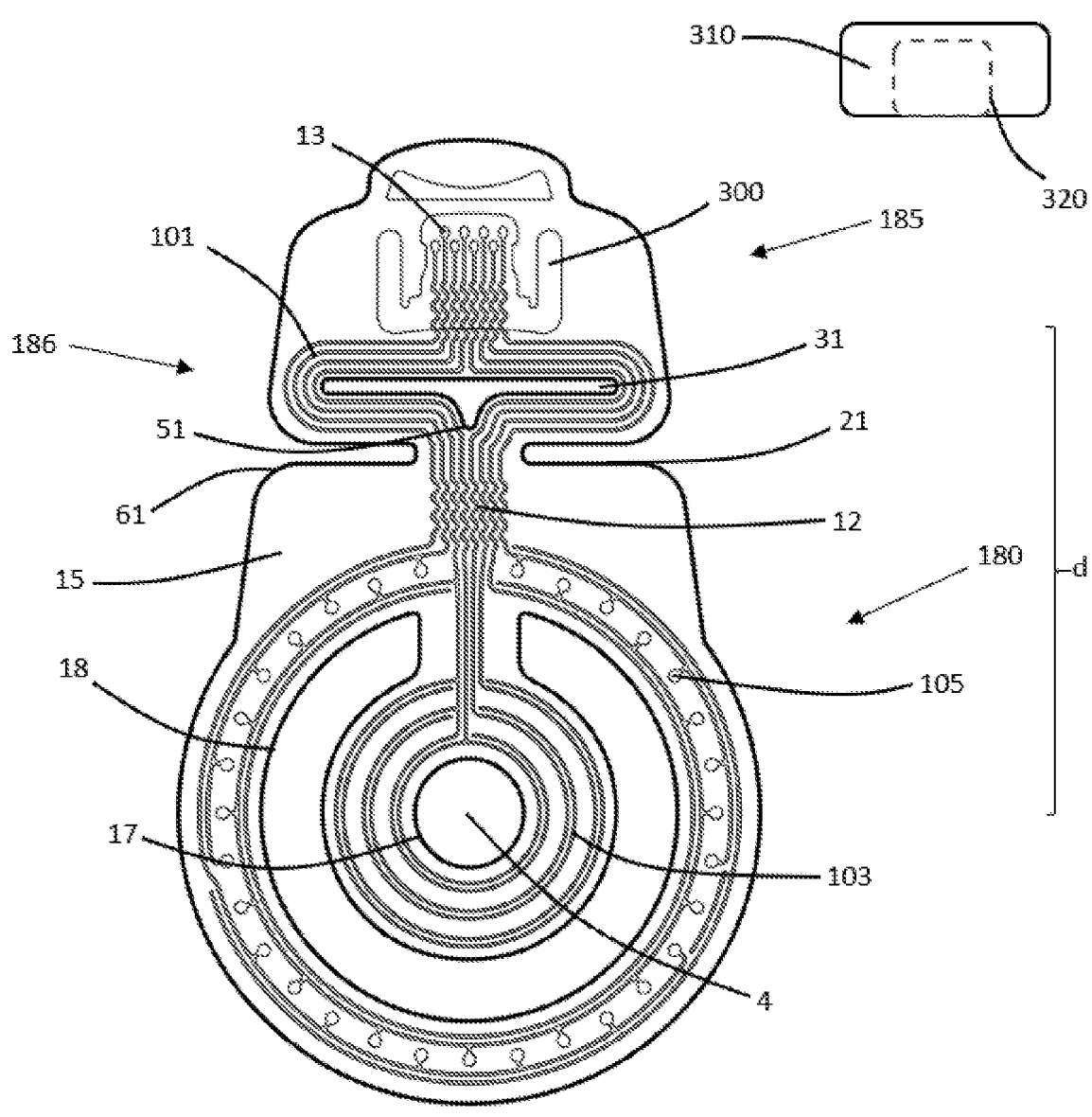
FIG. 6 illustrates a distal view of a sensor patch.

FIG. 6 illustrates an embodiment of the sensor patch 10 for attachment to a base plate for an ostomy appliance. The sensor patch 10 comprises a distal side 16 and a proximal side 14, which comprises at least one adhesive layer 15. The sensor patch comprises a circular-shaped central portion 180 and a neck portion 185. The neck portion has a length corresponding to a distance along the centre axis from the centre point of the central portion to the interface coupling of 40-110 mm, such as 60-90 mm, such as 70 mm.

The proximal adhesive side 14 is adapted to adhere to the skin surface of a user and the circular-shaped central portion is adapted for being attached to the base plate. The neck portion 185 extends radially outwards in one direction from the central section. The neck portion extends further than the outer rim of the base plate when the sensor patch is applied to such base plate, thereby leaving a part of the neck portion unattached to the base plate. The flexible element may overlap in radially direction with the outer rim of the base plate.

The sensor patch 10 comprises a layout of a plurality of electrodes 12. The electrodes 12 extend from the central portion 180 to the interface coupling 300 at the neck portion 185 via the flexible element 186. The flexible element 186 comprises a first row of two indents extending in parallel from the periphery towards the centre axis and a through-going aperture 31. The indents 21 and the through-going aperture 31 provide a z-shaped track for the electrodes 12.

The monitor interface 13 is configured for electrically and/or mechanically connecting the sensor patch 10 of the ostomy appliance (base plate 4) to the monitor device 310. The monitor interface 13 of the sensor patch comprises an interface coupling 300 for forming a mechanical connection, such as a releasable coupling between the monitor device 310 and the sensor patch. The interface coupling 300 is configured to engage with a complementary shaped coupling part of the monitor device for releasably coupling the monitor device to the sensor patch 10.

The periphery of the neck portion at the transition to the indents comprises a rounded outer edge 61.

The neck portion 185 comprises a flexible element 186 being adapted to allow the central portion 180 and the neck portion to be moved relative to each other. The flexible element 186 is positioned juxtaposed the central portion of the sensor patch.

The sensor patch comprises a plurality of electrodes 12 extending from the central portion 180 to the neck portion 185. The spatial layout of the electrodes is adapted the shape of the sensor patch. The electrodes 12 comprise a z-shaped spatial layout 101 at the flexible element 186.

The elongated through-going aperture 31 of the flexible element comprises an indent 51 to form a T-shaped through-going aperture. The adhesive layer 15 of the flexible element forms a track similar in shape as the layout of the electrodes 12.

Further, the flexible element comprises two opposed positioned elongated indents 21. The indents and the through going hole extend in parallel in staggered manner. The two indents 21 comprise rounded edges at the periphery of the sensor patch.

Figure 7:
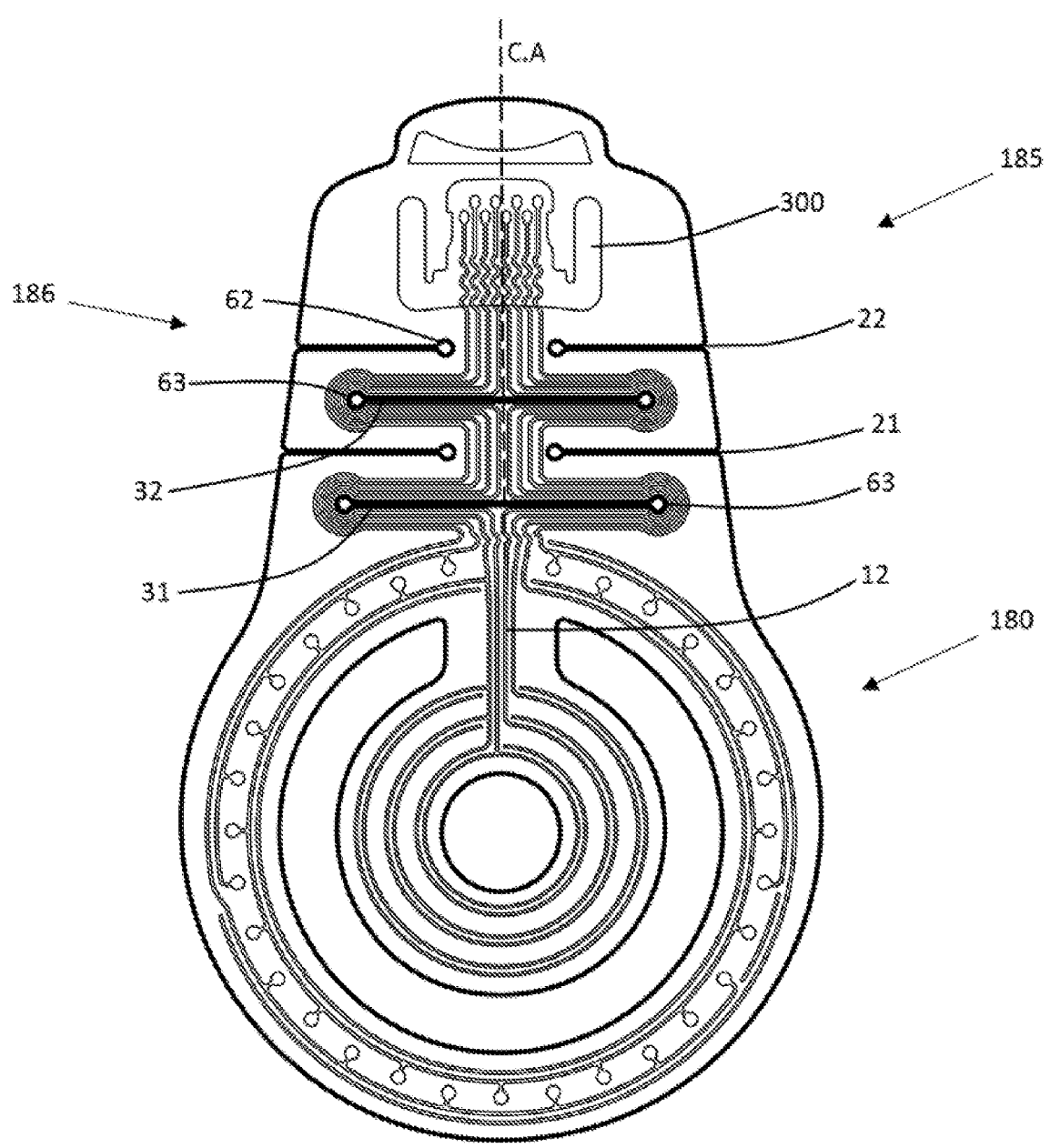
FIG. 7 illustrates a distal view of a sensor patch.

FIG. 7 illustrates a sensor patch 10 where the flexible element 186 comprises two elongated through-going slits 31,32 and two pairs of narrow elongated slits 21,22. The embodiment of the illustrated sensor patch comprises a flexible element 186 comprising two elongated through-going slits 31,32 arranged in a first set of two parallel rows. The flexible element 186 comprises four indents 21,22. The indents 21,22 extending inwards from the periphery of the neck portion towards the centre axis (C.A). The centre axis is illustrated as a dotted line which extends radially from the centre point 4 of the central portion to the interface coupling 300 adapted to be coupled with a monitor device at the neck portion.

The indents are perpendicular to the centre axis and are arranged in a second set of two parallel rows. The first set and second set of rows are positioned intermediate each other. Every other row being offset with respect to interme-diate rows as to form an accordion-shaped or zig zag-shaped pattern forming a track for the electrodes 12. At least part of the electrodes comprises a zig zag layout or similar pattern to form flexible electrodes.

The two elongated through-going slits 31,32 and the four narrow elongated indents 21,22 have rounded edges at the ends of the slits.

The neck portion is symmetrically shaped along the centre axis.

The central portion 180 is provided with a stomal opening 17 for receiving a stoma. A through going opening 18 partly encircling the stomal opening.

In embodiments, the sensor patch comprises a central portion. The central section is provided with a stomal opening. When the sensor patch is applied to a base plate, the stomal opening may be arranged substantially concentric to a stomal opening in the base plate, the opening being accommodated for receiving a stoma. In embodiments, the central section has a substantially circular or oval shape.

The invention claimed is:

1. A sensor patch adapted for attachment to a base plate for an ostomy appliance, the sensor comprising:
   - a distal side;
   - a proximal side comprising at least one adhesive layer, a part of the distal side is adapted for attachment to the base plate and the at least one adhesive layer of the proximal side is adapted to adhere the senor patch to skin of a user;
   - a central portion provided with an opening adapted for placement around a stoma;
   - a neck portion extending from the central portion, wherein the neck portion is symmetrically shaped rela-tive to a center longitudinal axis of the neck portion;
   - a monitor interface disposed on the neck portion, the monitor interface including a part adapted for releas-ably and mechanically coupling with a monitor device;
   - a flexible element located between the central portion and the neck portion and comprising a first pair of indents including a first indent formed as a first slit cut laterally into a periphery on a first side of the flexible element and extending toward the longitudinal axis of the neck portion and a second indent formed as a second slit cut laterally into a periphery on a second side of the flexible element and extending toward the longitudinal axis of the neck portion, with the first indent parallel to the second indent;
   - a first aperture formed through the flexible element, with the first aperture located within the periphery of the flexible element, where the first pair of indents and the first aperture of the flexible element allow the central portion and neck portion to flex and move relative to each other; and
   - a plurality of electrodes secured to the sensor patch around the opening in the central portion and secured to the sensor patch on the flexible element and secured to the sensor patch on the neck portion.

2. The sensor patch according to claim 1, wherein the first aperture formed through the flexible element is an elongated non-circular through-going aperture.

3. The sensor patch according to claim 1, wherein each of the first pair of indents is an elongated slit formed through a thickness of the neck portion.

4. The sensor patch according to claim 1, further com-prising a separate second pair of indents, with the second pair of indents comprising a third indent and a fourth indent, with the third indent parallel to the fourth indent and parallel to the first indent.

5. The sensor patch according to claim 1, wherein the first pair of indents and the first aperture are perpendicular relative to the centre longitudinal axis of the neck portion.

6. The sensor patch according to claim 1, further com-prising a second aperture formed between the first aperture and the monitor interface, with the second aperture located within the periphery of the flexible element.

7. The sensor patch according to claim 1, wherein the first indent and the first aperture comprise rounded edges.

8. The sensor patch according to claim 1, wherein the at least one adhesive layer comprises a first adhesive layer and a second adhesive layer that is different from the first adhesive layer.

9. The sensor patch according to claim 8, wherein the first adhesive layer covers at least part of the central portion and the second adhesive layer covers at least part of the neck portion.

10. The sensor patch according to claim 9, wherein the second adhesive layer extends in radial direction towards the central portion of the sensor patch and overlaps the first adhesive layer of the central portion and an outer rim of the base plate when the sensor patch and the base plate are adhered together.

11. The sensor patch according to claim 1, wherein an outer contour of the sensor patch comprises a pear-shape with the neck portion being narrower than the central portion.

12. The sensor patch according to claim 1, wherein the plurality of electrodes is disposed on the neck portion in a z-shaped layout pattern to form flexible electrodes.

* * * * *